US011759432B2

United States Patent
Giuliani et al.

(10) Patent No.: US 11,759,432 B2
(45) Date of Patent: *Sep. 19, 2023

(54) COMPOUNDS FOR PREVENTING AND TREATING SKIN OR MUCOSAL AFFECTIONS HAVING AN INFLAMMATORY COMPONENT

(71) Applicant: GIULIANI S.P.A., Milan (IT)

(72) Inventors: Giammaria Giuliani, Montagnola (CH); Ralf Paus, Hamburg (DE); Jeremy Cheret, Muenster (DE); Barbara Marzani, Carbonara Al Ticino (IT); Sergio Baroni, Vilia d'Adda (IT)

(73) Assignee: GIULIANI S.P.A., Milan (IT)

( * ) Notice: Subject to any disclaimer, the term of this patent is extended or adjusted under 35 U.S.C. 154(b) by 47 days.

This patent is subject to a terminal disclaimer.

(21) Appl. No.: 17/057,814

(22) PCT Filed: May 21, 2019

(86) PCT No.: PCT/EP2019/063143
§ 371 (c)(1),
(2) Date: Nov. 23, 2020

(87) PCT Pub. No.: WO2019/224211
PCT Pub. Date: Nov. 28, 2019

(65) Prior Publication Data
US 2022/0071921 A1    Mar. 10, 2022

(30) Foreign Application Priority Data
May 22, 2018   (IT) .................. 102018000005585

(51) Int. Cl.
| | |
|---|---|
| *A61K 31/045* | (2006.01) |
| *A61P 17/00* | (2006.01) |
| *A61P 29/00* | (2006.01) |
| *A61K 8/34* | (2006.01) |
| *A61Q 19/00* | (2006.01) |
| *A61Q 15/00* | (2006.01) |

(52) U.S. Cl.
CPC .............. *A61K 31/045* (2013.01); *A61K 8/34* (2013.01); *A61P 17/00* (2018.01); *A61P 29/00* (2018.01); *A61Q 15/00* (2013.01); *A61Q 19/00* (2013.01); *A61Q 19/007* (2013.01)

(58) Field of Classification Search
CPC .................. A61Q 19/00; A61P 17/00
See application file for complete search history.

(56) References Cited

U.S. PATENT DOCUMENTS

| 5,759,556 A * | 6/1998 | Burger .................. A61K 7/48 |
| | | 424/401 |
| 2005/0101678 A1* | 5/2005 | Natsch ................. A61Q 19/00 |
| | | 514/715 |

FOREIGN PATENT DOCUMENTS

| EP | 0955035 A1 * | 9/2004 | .............. A61K 7/32 |
| EP | 2245045 A1 | 11/2010 | |
| WO | 0108649 A1 | 2/2001 | |
| WO | WO2015193262 A1 * | 12/2015 | ........... A61K 31/045 |

OTHER PUBLICATIONS

Organica Aromatics, Sandanol, downloaded in Apr. 2022 (Year: 2022).*
A. P. Wood, Skin Microbiology, Body Odor, and Methylotrophic Bacteria, Handbook of Hydrocarbon and Lipid Microbiology, 2010 (Year: 2010).*
David J. MacGregor, Acne Vs. Rosacea, 450derm, How to tell Acne and Rosacea apart, downloaded in Jun. 2022 (Year: 2022).*
American Hair Loss Council, Folliculitis Can Cause Permanent Hair Loss, American Hair Loss Council, publication date: Mar. 26, 201 (Year: 2018).*
WO2015193262A1, Google English Translation, downloaded in Jun. 2022 (Year: 2022).*
International Preliminary Report on Patentability for PCT/EP2019/063143, dated Aug. 21, 2020.
International Search Report and Written Opinion for PCT/EP2019/063143, dated Sep. 11, 2019.

* cited by examiner

*Primary Examiner* — Mark V Stevens
*Assistant Examiner* — Alparslan Asan
(74) *Attorney, Agent, or Firm* — Troutman Pepper Hamilton Sanders LLP (Rochester)

(57) ABSTRACT

The present invention concerns the use of selected compounds in a cosmetic skincare treatment or in the treatment of certain skin, scalp or mucosal diseases. The invention also provides a composition for topical use incorporating a pharmaceutically or cosmetically effective amount of a compound for preventing or treating skin or mucosal diseases having an inflammatory component or for reducing the redness or irritation of skin or mucosae.

2 Claims, 1 Drawing Sheet

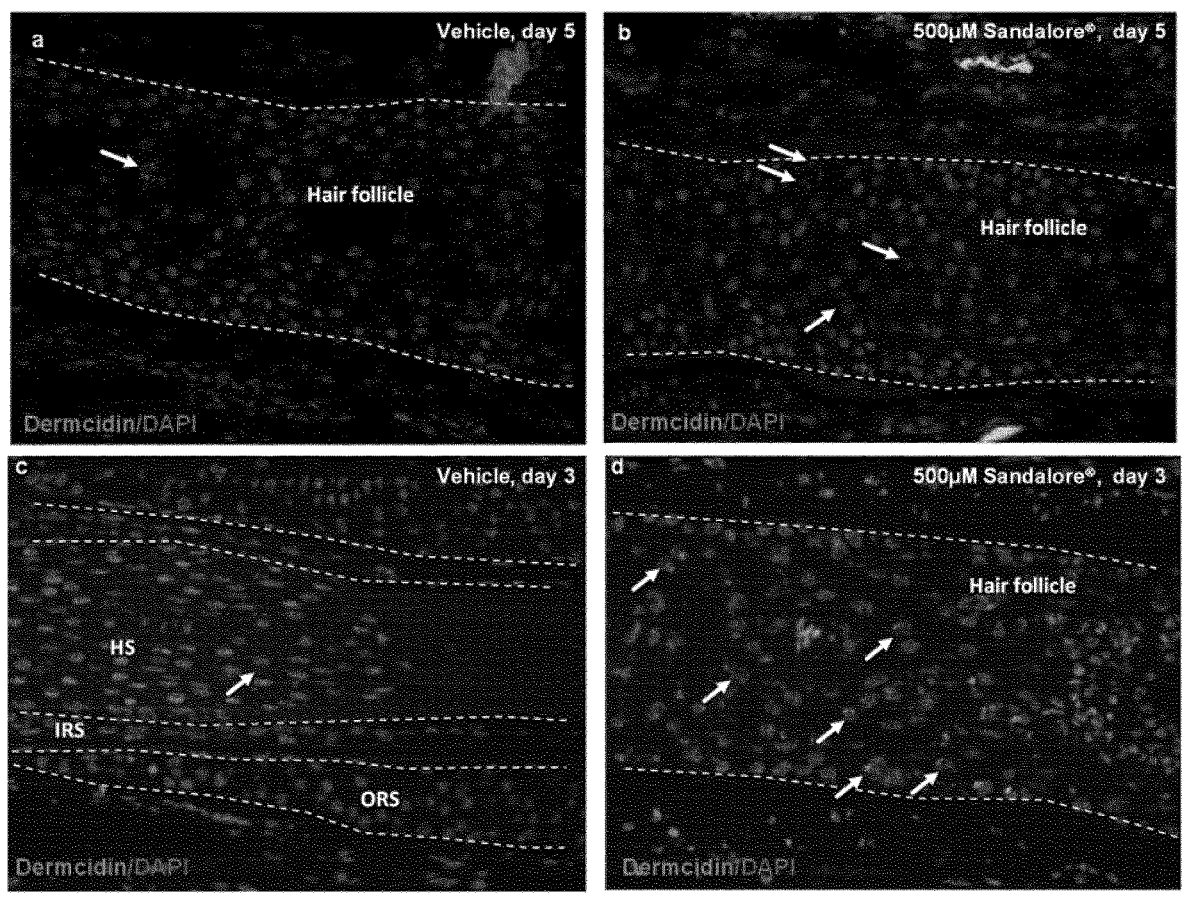

COMPOUNDS FOR PREVENTING AND TREATING SKIN OR MUCOSAL AFFECTIONS HAVING AN INFLAMMATORY COMPONENT

FIELD OF THE INVENTION

The invention concerns compounds for preventing or treating skin or mucosal affections.

The present invention origins in the field of cosmetic or pharmaceutical products for topical use.

Specifically, the present invention concerns the topical use of certain compounds for the cosmetic skincare treatment of cutaneous conditions or the dermatological treatment of certain skin, scalp or mucosal diseases in which an inflammation component plays a role.

PRIOR ART

The human skin forms a protective shield or mechanical barrier protecting the body and inner tissues from the aggression of external agents.

The skin is an ecosystem composed of diverse habitats with an abundance of folds, invaginations and specialized niches supporting a wide range of microorganisms.

The skin is also an interface with the outside environment and is colonized by a large number of different microorganisms. Most of these microorganisms are harmless and in some cases provide vital functions that the human genome has not evolved. Symbiotic microorganisms occupy a wide range of skin niches and protect against invasion by more pathogenic or harmful organisms. These microorganisms may also have a role in educating the T cells of the skin, priming them to respond to similarly marked pathogenic microorganisms.

To defend against pathogens, the cell of the skin and dermis possess a defense immune response. The immune response of the skin is innate and plays the following major roles: recognize the pathogenic microorganisms, induce the production of specific molecules fighting against the pathogens, and secrete specific peptides to directly kill the pathogenic microorganisms. Antimicrobial peptides also referred as AMPs, are peptides having a broad spectrum antimicrobial activity against bacteria, virus and fungi which play an important role against infections especially of the skin. Typically, these peptides are cationic and usually are 20 to 60 amino acids in length.

The cationic nature of these peptides allow them to bind to negatively charged molecules of the bacterial membrane such as lipopolysaccharides.

In addition AMPs are provided with hydrophobic and hydrophilic sides which enable them to interact in the aqueous environmental and with lipid membranes.

These peptides, in addition to their antimicrobial activity also exert a function against the host cells themselves and have the capability of alerting host cells to the potential for infections or the presence of skin injuries.

In addition, the antimicrobial peptides also acts on host cells to stimulate cytokine production, cell proliferation, and extracellular matrix synthesis.

The production of antimicrobial peptides by human epidermis such as defensins and cathelicidins, which occurs constitutively, greatly increases in case of infections or skin injury.

It has been observed that certain skin diseases show altered expression of AMPs, a phenomenon that partially explains the pathophysiology of these diseases.

Accordingly, the current research suggests that understanding how antimicrobial peptides modify susceptibility to microbes influences certain skin conditions and provides insight into the origins of certain disorders.

Nevertheless, the etiopathogenesis of a certain number of skin diseases is multifactorial such as in the case of psoriasis, atopic dermatitis, rosacea, acne, acne inversa/hidradenitis suppurativa and others, and do not seem strictly correlated with an altered expressions of AMPs and to their antimicrobial activity.

Therefore, there is still a need of investigating the etiology of certain skin diseases especially those which are not derivable from infections or dysregulation of those beneficial bacterial species colonizing the skin to find out suitable products which are effective in the treatment of skin disorders or conditions having a multifactorial etiology and an inflammatory component.

In view of the above, one of the aim of the present invention consists in the provisions of compounds for the prevention and/or treatment of skin conditions in which inflammation plays a role.

Another aim of the invention resides in providing products for dermatological use which represents therapeutic opportunities different from the available skin care products of medicines.

A further aim of the invention resides in the provision of cosmetic products which are useful in ameliorating the aspect of the skin, especially skin of the face affected by mild acne or redness.

SUMMARY OF THE INVENTION

In accordance with a general aspect of the present invention, the inventors have found that certain selected compounds of following formula (I) when are applied on the skin exert a topical immunostimulating action which determines a reduction of the inflammation of the skin and are useful in the treatment of skin conditions or diseases wherein the inflammatory component plays a role.

The inventors also observed that the topical anti-inflammatory action exerted by the selected compounds of the invention is mediated by the peptide dermcidin.

Thus, in accordance with a first aspect, compounds of formula (I) are provided

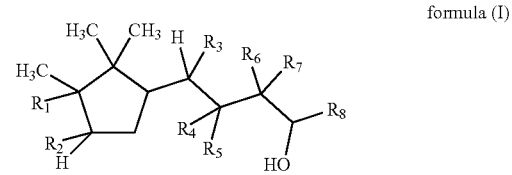

formula (I)

wherein:

$R_1$ and $R_2$ form together a double bond, or $R_1$ and $R_2$ form together a cyclopropyl group;

$R_3$, $R_4$ are the same or different and independently selected from hydrogen, methyl, or $R_3$ and $R_4$ form together a double bond;

$R_5$, $R_6$ are the same or different and independently selected from hydrogen, methyl; or $R_5$ and $R_6$ form together a double bond, or $R_5$ and $R_6$ form together a cyclopropyl group;

$R_7$=methyl, or ethyl;

$R_8$=hydrogen, or methyl, for use in the prevention or treatment of skin diseases in which the inflammatory component plays a role wherein the skin diseases are selected from the group consisting of psoriasis, rosacea, folliculitis and bromhidrosis.

Typically, the skin diseases treated by the topical application of the compounds of formula (I) are skin diseases with an inflammatory components, especially those referred herein below.

In accordance with a second aspect the present invention provides the cosmetic use of a compound of formula (I) as defined above as cosmetic skincare treatment.

In accordance with this second aspect the cosmetic use of a compounds of formula (I) is provided for ameliorating the aesthetic aspect offlushed skin, red skin or skin rashes.

In accordance with an embodiment the compound of formula (I) are useful for reducing skin reddening.

In accordance with an additional aspect compositions are provided for topical application comprising an effective amount of a compound of formula (I) as defined above and a cosmetically or pharmaceutically acceptable carrier.

Certain aspects and advantages of the invention are further described with reference to the appended drawings.

BRIEF DESCRIPTION OF THE DRAWING

FIG. 1 shows dermcidin protein expression in the epithelium of human scalp Hair Follicles (HFs) with Sandalore treatment Representative images show dermcidin (white arrows) in Sandalore and vehicle human treated scalp microdissected hair follicle for 5 days (a,b) or 3 days (c,d) ex vivo. Qualitative observation deriving from the analysis of n=3 independent experiments (3 donors) (a,b) or 1 independent experiment (1 donor) (c, d). HS, hair shaft; IRS, inner root sheath; ORS, outer root sheath.

The experimental data indicate the number of positive cells (DCD+cells). In the vehicle are present 4.444±0.623 (mean±SEM) DCD+ cells, whereas in the treatment with 500 microM the DCD+ cells are 7.786±0.596 (mean±SEM). Sandalore induces statistical significant increase of the number of DCD+ cells with respect to vehicle (p<0.001).

DETAILED DESCRIPTION OF THE INVENTION

According to certain aspects of the invention, the inventors founds that specific compounds activate certain immune defense mechanisms of the skin and/or promote an immune-stimulating activity which is mediated by dermcidin, a peptide which is constitutively secreted in human sweat and which typically plays a role in the regulation of the innate immune response as evidenced by Echo Wang et al. on Shock, 2016 January; 45(1): 28-32.

In accordance with a first aspect the present invention provides compounds of formula (I) for use as claimed in appended claim 1.

Further embodiments of the pharmaceutical use of compounds of formula (I) invention are defined in appended claims 2-4.

Compounds of formula (I) were developed as synthetic substitutes of natural sandalwood. They provide a fragrance similar to that of Sandalwood.

In general, the terminology sandalwood is referred to a class of woods from trees of the genus Santalum. The essential oil of sandalwood commonly is extracted by steam distillation of wood from matured sandalwood trees, and is a well-known valued component for perfumes.

The main components of sandalwood oil are α-santalol e β-santalol, which are alcohols basically showing a sesquiterpenic type chain.

The structural formula of α-santalol is the following

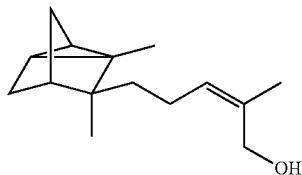 [SMILES: C/C(=C/CCC1(C)C2CC3C(C2)C31C)CO]

The structural formula of β-santalol, which is as follow,

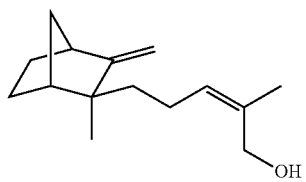 [SMILES: C=C1C2CCC(C2)C1(C)CC/C=C(/C)CO]

The above chemical structures includes a terminal tricyclohept-3-yl or a bicyclohept-2-yl group, respectively.

One of the preferred compounds for the topical uses according to the invention is sandal pentanol, also known as Sandalore®. This is a synthetic odorant having a fragrance similar to sandalwood and commonly used as component of perfumes or as emollient or skin cleaning agent or as an ingredient mimicking the sandalwood scent.

Typically, Sandalore, and its analogue derivatives, are alcohols having a chemical structure different from α-santalol e β-santalol which origin from natural sandalwood oil.

Sandalore, or sandal pentanol, have the following formula:

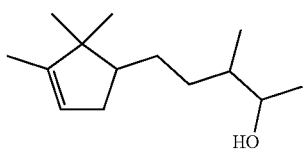

Typically, the above referred molecules are synthetic.

In accordance with certain embodiments the compounds of formula (I) contain a terminal cyclopenten-1-yl group and have no polycyclic structure typical of natural sandalwood oil constituents.

In accordance with certain embodiments, the compounds of formula (I) are selected from the compounds illustrated in the following Table:

| Compound | IUPAC Name | CAS No | Structural formula | Formula/MW |
|---|---|---|---|---|
| 1 sandal pentanol | 3-methyl-5-(2,2,3-trimethylcyclopent-3-en-1-yl)pentan-2-ol | 65113-99-7 | | $C_{14}H_{26}O$ 210.36 |
| 2 sandal pentenol | (4Z)-3-methyl-5-(2,2,3-trimethylcyclopent-3-en-1-yl)pent-4-en-2-ol | 67801-20-1 | | $C_{14}H_{24}O$ 208.35 |
| 3 sandal cyclopropane | 1-methyl-2-((1,2,2-trimethylbicyclo(3.1.0)hex-3-yl)methyl)-cyclopropane-methanol | 198404-98-7 | | $C_{15}H_{26}O$ 222.37 |
| 4 Santol pentenol | (E)-3,3-dimethyl-5-(2,2,3-trimethylcyclopent-3-en-1-yl)pent-4-en-2-ol | 107898-54-4 | | $C_{15}H_{26}O$ 222.37 |
| 5 sandal cyclopentane | 2-Methyl-4-(2,2,3-trimethyl-3-cyclopenten-1-yl)butanol | 72089-08-8 | | $C_{13}H_{24}O$ 196.34 |
| 6 sandalrome | (E)-2-ethyl-4-(2,2,3-trimethylcyclopent-3-en-1-yl)but-2-en-1-ol | 28219-61-6 | | $C_{14}H_{24}O$ 208.35 |
| 7 sandal butenol | (E)-2-methyl-4-(2,2,3-trimethyl-3-cyclopenten-1-yl)-2-buten-1-ol | 28219-60-5 | | $C_{13}H_{22}O$ 194.32 |

A preferred compound falling in formula (I) and illustrated in the above Table is sandal pentanol (compound 1).

In accordance with certain embodiments the compounds of formula (I) have a 2,2,3-trimethylcyclopent-3-en-1yl moiety bearing a $C_4$-$C_5$ alkyl or $C_4$-$C_5$ alkenyl group in the 1-position of the ring. Preferred compounds falling in this embodiments are those with the moiety bearing a $C_4$-$C_5$ alkyl group in the 1-position of the ring, for example compounds 1, 2, 4, 5, 6, 7 referred in the above Table.

In accordance with certain embodiments, sandal cyclopentane is excluded from the compounds of formula (I).

It has been found that the selected compounds of formula (I) or the compounds falling in anyone of the above referred embodiments, when applied on the skin activates or promotes an immune defense response or an immune modulation action which is at the basis of their anti-inflammatory action.

Typically, the referred immune modulation action is mediated by dermcidin (DCD), a protein secreted by eccrine gland.

In contrast to antimicrobial peptides (AMPs), dermcidin is constitutively secreted in human sweat and is not inducible by inflammation or skin injury.

In addition, contrary to the more common AMPs, such as defensins and cathelicidin, which are cationic peptides which bind to and permeabilize the bacterial membranes, dermcidin is an anionic peptide and kill bacteria through a different molecular mechanism.

These properties make the dermcidin-mediated anti-inflammatory activity of the selected compounds of formula (I) in skin diseases underivable from the antimicrobial peptides having cationic nature allowing them to bind and disrupt bacterial membrane molecules.

Medical Uses

The inventors have also evidenced that the application on the skin of compounds of formula (I) stimulates the expression of dermcidin, a specific peptide provided with a local/topical anti-inflammatory action.

These compounds exert an action on inflammatory skin diseases which makes them useful in the treatment of certain skin diseases with an inflammatory component especially psoriasis, folliculitis, rosacea and bromhidrosis especially severe bromhidrosis.

The compounds of formula (I) are also useful in the treatment of bromhidrosis because one of the factor from which this disorder origins is the dysregulation of skin secretion from eccrine sweat glands which are regulated by dermcidin which is the biological target of compounds of formula (I).

It has been also observed that the topical application to the skin of the compounds of formula (I) alters the composition of the microbiome from a pathological to healthy state thus resulting effective in many different skin diseases wherein inflammation is a component.

In accordance with these aspects, a therapeutically effective amount of a pharmaceutical composition containing a compound of formula (I) is applied on the area of the skin in need of treatment. The treatment may include the application of the composition at least once a day, preferably twice until full recovery or until the symptomatology of the related diseases is substantially reduced or resolved.

The present disclosure also provides a method of treatment of inflammatory diseases of the skin said method comprising the topical administration of an effective amount of a compound of formula (I) or a composition containing said compound and a pharmaceutically acceptable carrier.

In accordance with this aspect, the method is useful in the treatment of folliculitis.

The methods and compositions disclosed herein may be used for a wide range of skin disorders in which an inflammatory component is present including psoriasis, rosacea and folliculitis.

Problems with current treatments for these disorders include antibiotic resistance, side effects, complicated regimens, and lack of long-term effectiveness. Treatments disclosed herein may provide alternatives to antibiotic and/or anti-inflammatory therapy, the use of compounds of formula (I) according to the invention, presenting very few or absence of side effects with simple treatment regimens and long-term effectiveness.

Cosmetic Uses

It has been observed that the compounds of formula (I) ameliorated the aesthetic aspect of flushed skin, red skin, skin rashes and the redness of skin.

Thus, in accordance with another aspect of the invention the cosmetic, non-therapeutic use of compounds of formula (I) as cosmetic skincare treatment is provided in accordance with claims 5 to 10.

In accordance with some embodiments it is provided the cosmetic, non therapeutic, use of compounds of formula (I) for the topical prevention and/or treatment of imperfection or blemish of the skin, for example for ameliorating the aesthetic aspect of flushed skin, or for reducing skin rashes or discoloring red skin or blotches.

Within the cosmetic uses of the compounds of formula (I) or composition containing the same, also fall mild acne and the excessive sebum production.

The term "cosmetically acceptable" as used herein means that the components of the compositions are suitable for cutaneous or mucosal application in general, and when applied they do not cause an unwanted toxicity, allergic response, redness, incompatibility, instability, and similar reactions.

Compositions

In accordance with another aspect of the invention, a composition is provided, comprising an effective amount of one of the compounds of formula (I) according to anyone of the embodiments referred herein above and a physiologically acceptable carrier.

The composition may be a pharmaceutical composition or a cosmetic composition. A suitable carrier is a pharmaceutically, phisiologically or cosmetically acceptable carrier.

Typically, the composition are suitable for topical application on the skin or on mucosa.

In the present specification, the term "carrier" refers to an excipient, carrier, diluent or adjuvant which has no activity and which may be present in the composition of the invention. Any carrier and/or excipient suitable for the form of preparation desired for administration is contemplated in the uses described herein.

Typically, cosmetically acceptable carrier are used for the cosmetic uses of the compounds of formula (I) of the invention.

In accordance with certain embodiments, the composition of the invention contains a pharmaceutically acceptable and/or physiologically acceptable carrier or, and a compound of formula (I) in an amount ranging from 0.1 to 20% by weight, from 0.5 to 15%, from 1 to 10% by weight.

Typically, the composition of the invention either for cosmetic and pharmaceutical uses are in any forms suitable for topical/local application and may be in solid, fluid or semifluid form.

Suitable compositions in solid form comprise creams, pastes, ointments, gel, bandages for pharmaceutical or cosmetic applications and sticks, make-up.

In accordance with a preferred embodiment, the composition is a cream for topical application.

Suitable compositions in fluid form include water-based formulations such as suspensions, solutions, lotions, gels, shampoos.

Suitable compositions in semi-fluid form include foams and emulsions.

For cosmetic application suitable forms include masks, transdermal paste or patch. In the composition of the invention, one or more excipients typically used in the basic formulation of pharmaceutical or cosmetic formulations may be incorporated, such as oils, glycerin, emollients, emulsifiers, dispersing agent, in amounts which are typical for the desired use.

In the formulation of the composition of the invention may be present additional ingredients such as a Bisabolol, inositol, betaine, allantoins, ceramides for the creamy formulation.

In some embodiments, the fluid or semifluid composition of the invention may contain lipophilic substances such as oils, for example Hydrogenated castor oil.

In the case of formulations in liquid form, water is present as a diluent or solvent, optionally mixed with other liquids used for the formulation of pharmaceutical or cosmetic compositions.

According to another embodiment, the cosmetic composition further comprises one or more amongst thickeners, solubilizers, preservatives, water, alcohols, glycerin, stabilizers, cosmetically acceptable antioxidants and antibacterials in amounts according to the common pharmaceutical or cosmetic practice.

The present description is further described herein below with reference to the following examples which represent embodiments of the invention.

Example No. 1

Cream

| Component | Q.ty (% w/w) |
|---|---|
| PEG-8 Beeswax | 6-18 |
| Octyldodecanol | 4-11 |
| Diisopropyl sebacate | 3-8 |
| Mixed triglyceirdes decanoyl and octanoyl | 2.3-6.8 |
| Isostearyl isostearate | 2-6 |
| Sandalore (sandal pentanol) | 1-2 |
| Butyrospermum parkii butter | 1-3 |
| Dicaprylyl ether | 1-3 |
| Pentylene glycol | 1-3 |
| Glycerin | 1-2 |
| Polymethyl methacrylate | 1-2 |
| Potassium cetyl phosphate | 1-2 |
| Symdiol 68T | 0.4-1.1 |
| Alphaa Bisabolol | 0.3-0.8 |
| Betaine monohydrate | 0.3-0.8 |
| Inositol | 0.3-0.8 |
| Trehalose 100 | 0.3-0.8 |
| Poloxamer 407 | 0.18-0.53 |
| Dissolvine GL-38 | 0.2-0.5 |
| Carbomer | 0.1-0.3 |
| Hydrogenated soy lecithin | 0.1-0.3 |
| Oxynex ST Liquid | 0.1-0.3 |
| Tromethamine | 0.09-0.27 |
| Allantoin | 0.08-0.23 |
| Disodium EDTA dihydrated | 0.1-0.2 |
| Pentaerytritol Tetrakis (3-(3.5-di-tert-butyl-4 hydroxyphenyl) propionate | 0.03-0.08 |
| Lactic acid 80% | 0.018-0.053 |
| Dimethylmethoxy chromanol | 0.01-0.03 |
| Water | q.s. to 100 g |

Example No. 2

Lotion

| Component | Q.ty (% w/w) |
|---|---|
| Ethanol | 10-20 |
| Disodium EDTA | 0.03-0.09 |
| PEG-40 Hydrogenated castor oil | 0.75-2.25 |
| Sandalore (sandal pentanol) | 0.5-2.5 |
| Water | q.s. to 100 g |

Example No. 3

Deodorant

| Component | Q.ty (% w/w) |
|---|---|
| Ethanol | 20-30 |
| Sandalore (sandal pentanol) | 0.1-10.0 |
| PEG-40 Hydrogenated castor oil | 1-3 |
| Tocopheryl acetate | 0.1-0.2 |
| D-Panthenol | 0.3-0.8 |
| 1.2 Propandiol | 5-15 |
| Triethyl citrate | 0.2-0.5 |
| Water | q.s. to 100 g |

Example No. 4

Body cream

| Component | Q.ty (% w/w) |
|---|---|
| Isopropyl myristate | 5-10 |
| Polisorbato 60 | 4.5-7.5 |
| Sandalore (sandal pentanol) | 0.1-10.0 |
| Sodium hydroxide | 0.05-0.15 |
| Alcool benzilico | 1-2 |
| Sorbitan monostearate | 1.5-2.5 |
| Cetyl palmitate | 2-3 |
| Cetyl alcohol | 3-5 |
| Stearyl Alcohol | 3-5 |
| Water | q.s. to 100 g |

Example No. 5

Face cream

| Component | Q.ty (% w/w) |
|---|---|
| C12-13 alkyl lactate | 3-5 |
| Gemseal 25 | 3-5 |
| Sandalore (sandal pentanol) | 0.1-10.0 |
| PEG-30 Dipolyhydroxystearate | 1.3-3.8 |
| Magnesium sulphate heptahydrate | 0.4-1.2 |
| Silica dimethyl silylate | 1-2 |
| Hydrogenated castor oil | 1-2 |
| Super sterol esters | 0.3-0.8 |
| Ethylhexyl palmitate | 3-8 |
| Allantoin | 0.1-0.3 |
| Fenossiethanol | 0.4-0.6 |
| Glycerin | 2.3-6.8 |
| PPG-15 Stearyl ether | 1-3 |
| Nylon-12 | 1-3 |
| Ceramide Omega 9 | 0.1-0.3 |
| Collageneer | 0.2-0.5 |
| Water | q.s. to 100 g |

Example No. 6

Spray solution

| Component | Q.ty (% w/w) |
|---|---|
| Ethanol | 30-50 |
| Propylene glycol | 2.5-8.0 |
| Sandalore (sandal pentanol) | 0.1-10.0 |
| Water | q.s. to 100 g |

Example No. 7

Vaginal solution

| Component | Q.ty (% w/w) |
|---|---|
| Poloxamer | 30-50 |
| Propylene glycol | 30-50 |
| sandalore | 0.1-10 |
| water | q.s. to 100 g |

Example No. 8

Experimental evidence of regulation (promotion) of dermcidin by sandal pentanol. This experimental evidence is also based on the antinflammatory activity of dermcidin as evidenced in the article "*The in vitro immune modulating properties of a swedt gland-derived anti-microbial peptide dermcidin*" to Echo Wang et al., published on Shock, 2016 January; 45(1): 28-32.doi.1097/SHK0000000000000488, especially FIG. 3 showing that dermcidin modulated LPS- and HMGB1-induced chemokine (pro-inflammatory cytokines) release by human monocytes.

HF Organ Culture:

Human scalp samples were obtained 1 day after face-lifting procedure (i.e. after overnight transport from collaborating surgeons) and used at the same day for microdissecting human anagen VI scalp HFs. The HF microdissection technique employed for setting up the classical Philpott assay used in the current study, removes all perifollicular tissue with the sole exception of the HF's dermal sheath and thus does not contain any other skin appendage structures (e.g. eccrine gland elements). Microdissected human scalp HFs were cultured at 37° C. with 5% $CO_2$ in a minimal media of William's E media (WEM, Gibco, Life technologies) supplemented with 2 mM of L-glutamine (Gibco), 10 ng/ml hydrocortisone (Sigma-Aldrich), 10 µg/ml insulin (Sigma-Aldrich) and 1% penicillin/streptomycin mix (Gibco) (WEM). After microdissection, the HFs were first incubated in WEM for 24 hrs for re-equilibration.

Chemical Stimulation of Human Microdissected HFs with Sandal Pentanol

After 24 hours, WEM medium was replaced and HFs were treated with vehicle (0.1% DMSO), sandal pentanol 500 µM, for 3 or 5 days for (immuno-)histology or 6 hours for microarray. Culture medium was replaced every second day and after 6 days, HFs were then embedded in cryomatrix (Fisher Scientific), and snap frozen in liquid nitrogen for (immuno-)histology.

Microarray Analysis

Expressional alteration was considered to be significant only when ≥1.8-fold and equidirectional changes were observed in at least 3 of 4 patients (independent experiments).

Dermcidin Immunofluorescent Staining

OCT embedded samples were sectioned with a Leica cryostat. Dermicidin protein was detected using tissue sections fixed in 4% paraformaldehyde, pre-incubated with 10% of goat serum, and incubated with a mouse anti-human Dermcidin (Novus Biologicals, G-81, 1:200). Secondary antibody (Goat anti-mouse Alexa fluor 488) incubation was performed at room temperature for 45 min. Counterstaining with DAPI (1 µg/mL) was performed to visualize nuclei.

Results

Dermicidin protein expression is increased in hair follicle outer root sheath keratinocytes ex vivo after sandal pentanol (500 µM) treatment for 3 and 5 days (FIG. 1). Data are confirmed in following Table 1.

Microarray analysis revealed that Sandalore significantly promotes AMPs secretion since transcripts of AMPs genes were up-regulated, particularly Dermcidin expression increased by 77.6 folds.

TABLE 1

|  | Dermcidin positive cells | |
|---|---|---|
|  | Vehicle | 500 µM Sandalore |
| Mean | 4.444 | 7.786*** |
| SEM | 0.6232 | 0.5962 |

***$p < 0.001$

The invention claimed is:

1. A method of treating a skin, scalp, or mucosal inflammatory disease, said method comprising:
   administering topically, to a subject having a skin, scalp or mucosal inflammatory disease, sandal pentanol in an amount effective to promote anti-inflammatory activity mediated by dermcidin, wherein said disease is selected from the group consisting of psoriasis, rosacea, folliculitis, and skin rashes.

2. The method of claim 1, wherein the sandal pentanol is in a composition further comprising a physiologically acceptable carrier.